United States Patent
Banks

(10) Patent No.: US 7,628,823 B2
(45) Date of Patent: Dec. 8, 2009

(54) METHOD OF TESTING FOR ATP LOAD IN COMMERCIAL LAUNDRY AND FOR DATA TRACKING THE RESULTS

(75) Inventor: Allen G. Banks, Franklin, OH (US)

(73) Assignee: Washing Systems, LLC, Cincinnati, OH (US)

( * ) Notice: Subject to any disclaimer, the term of this patent is extended or adjusted under 35 U.S.C. 154(b) by 0 days.

(21) Appl. No.: 11/656,054

(22) Filed: Jan. 22, 2007

(65) Prior Publication Data

US 2008/0176250 A1    Jul. 24, 2008

(51) Int. Cl.
  *C12Q 1/66* (2006.01)
(52) U.S. Cl. .................... 8/137; 435/8; 134/10
(58) Field of Classification Search ........... 8/137; 435/8; 134/10
See application file for complete search history.

(56) References Cited

U.S. PATENT DOCUMENTS

| | | | |
|---|---|---|---|
| 2,165,884 A * | 7/1939 | Chamberlin et al. | 8/159 |
| 4,385,113 A | 5/1983 | Chappelle et al. | |
| 5,004,684 A | 4/1991 | Simpson et al. | |
| 5,811,251 A | 9/1998 | Hirose et al. | |
| 5,905,029 A | 5/1999 | Andreotti et al. | |
| 5,965,453 A * | 10/1999 | Skiffington et al. | 436/165 |
| 6,180,395 B1 | 1/2001 | Skiffington et al. | |
| 6,653,147 B2 | 11/2003 | DiCesare | |
| 7,132,249 B1 | 11/2006 | Salter et al. | |
| 2005/0070701 A1 | 3/2005 | Hochstetler et al. | |
| 2006/0010611 A1 | 1/2006 | Snow | |
| 2006/0170913 A1 | 8/2006 | Burke et al. | |
| 2009/0011457 A1 * | 1/2009 | Faeh et al. | 435/32 |

FOREIGN PATENT DOCUMENTS

WO   WO 2005/093085 A1 *  10/2005
WO   WO 2005/098019    *  10/2005

OTHER PUBLICATIONS

McCarthy, B. J. "Bioluminescent assay of microbial contamination on textile materials." International Biodeterioration & Biodegradation (2001), vol. 48, pp. 79-83.*
Internet Website, Charm Sciences, Inc.—Food Safety Technology http://www.charm.com—WaterGiene™; New Sensitive ATP Indicator for Water Quality Products: WaterGiene™; PocketSwab® Plus—Now with Room Temperature Stability; PocketH2O™—ATP Quality Test for Water; AllerGiene®—An ATP Based Food Cross-Contact Control.
Internet Website, Antimicrobial Specialists & Associates, Inc. (AMSA, Inc.) http://amsainc.com—Welcome to AMSA, Inc.; All-in-One Shot™ ATP Test Pens; Welcome to the World of ATP anaylsis; How to Interpret ATP Numbers.

* cited by examiner

*Primary Examiner*—Lorna M Douyon
*Assistant Examiner*—Amina Khan
(74) *Attorney, Agent, or Firm*—Sand & Sebolt

(57) ABSTRACT

A method of testing for sanitization of textiles comprises the steps of cleaning textiles in a water solution and testing the water solution for the presence of contaminants such as adenosine triphosphate (ATP), typically with a luminometer. Typically, the water solution will be drained from a cleaning vessel and tested. Another option is the testing of the water solution extracted after draining such as by a spin cycle. The method provides improved accuracy of test results as to the level of cleanliness. In addition, testing at this early step of the laundering process allows for additional cleaning if needed without having undertaken costly and time-consuming steps such as drying. Moreover, absent re-contamination of the textiles after the cleaning process, drying and finishing procedures may be accomplished without further sanitizing the textiles.

22 Claims, 3 Drawing Sheets

METHOD OF TESTING FOR ATP LOAD IN COMMERCIAL LAUNDRY AND FOR DATA TRACKING THE RESULTS

BACKGROUND OF THE INVENTION

1. Technical Field

The present invention relates generally to the laundering of textiles. More particularly, the invention relates to the insurance of an acceptable level of cleanliness of the textiles. Specifically, the invention relates to the testing of the water solution in which the textiles are cleaned for the presence of adenosine triphosphate (ATP).

2. Background Information

In the field of industrial laundering, there is a need to ensure that textiles which are laundered meet certain standards of cleanliness. Of particular concern is the amount of bacteria on the laundered textiles although the amount of other contaminants is also important. Testing for the presence of adenosine triphosphate (ATP) is a useful indicator of various contaminants including bacteria because ATP delivers energy to all living organisms and is found in organisms both living and dead.

One of the current primary test methods involves the direct testing of textiles which have been laundered and dried. In particular, test procedures have been developed which utilize a swab rubbed directly on textiles in order to obtain a test sample of ATP therefrom. A luminometer is then used to quickly analyze the concentration or amount of ATP on the swab. A test kit using such a swab is described in greater detail in U.S. Pat. No. 6,180,395 granted to Skiffington et al., which is incorporated herein by reference. This test method provides rapid results and thus is a great advantage over the relatively slow process of bacterial colony growth, which usually takes about two days and is obviously not suitable for the purposes of testing laundered textiles.

While such swabbing methods are very convenient, they nonetheless have some drawbacks. One disadvantage is that the testing occurs after the textiles have been dried. Thus, if a given piece or batch of textiles must be re-washed due to an unacceptable ATP level which remained after laundering, that piece or batch of textiles will have already undergone the costly and time consuming step of drying. In addition, the swab testing of a given textile may produce different results depending on where the textile is swabbed. More particularly, a given textile may have been heavily soiled in one area and lightly soiled in another area so that even after laundering, the area which was heavily soiled may retain a greater degree of contamination. In addition, in order to obtain a suitable sample size which is likely to be representative of a large batch of textiles, a fairly large number of textiles must be individually tested in the present swabbing method to minimize concerns related to random sampling. Thus, there is a need in the art to provide a test for sanitation of textiles at an earlier stage of the laundering process while minimizing the number of tests performed.

BRIEF SUMMARY OF THE INVENTION

The present invention provides a method comprising the steps of cleaning textiles with a water solution whereby the water solution becomes used; and testing the used water solution for the presence of adenosine triphosphate (ATP).

The present invention also provides a method comprising the steps of cleaning textiles with a water solution whereby the water solution becomes used; and testing the used water solution to determine a level of contaminants therein in no more than 15 minutes.

The present invention further provides a method comprising the steps of cleaning textiles with a water solution in a cleaning vessel whereby the water solution becomes used; and testing the used water solution to determine a level of contaminants therein while the textiles remain in the cleaning vessel.

DETAILED DESCRIPTION OF THE INVENTION

A first method of the present invention is described with reference to FIGS. 1-2; and a second method is described with reference to FIG. 3. Generally, the methods of the present invention are used to ensure the sanitation or cleanliness of laundered textiles.

Figure 1:
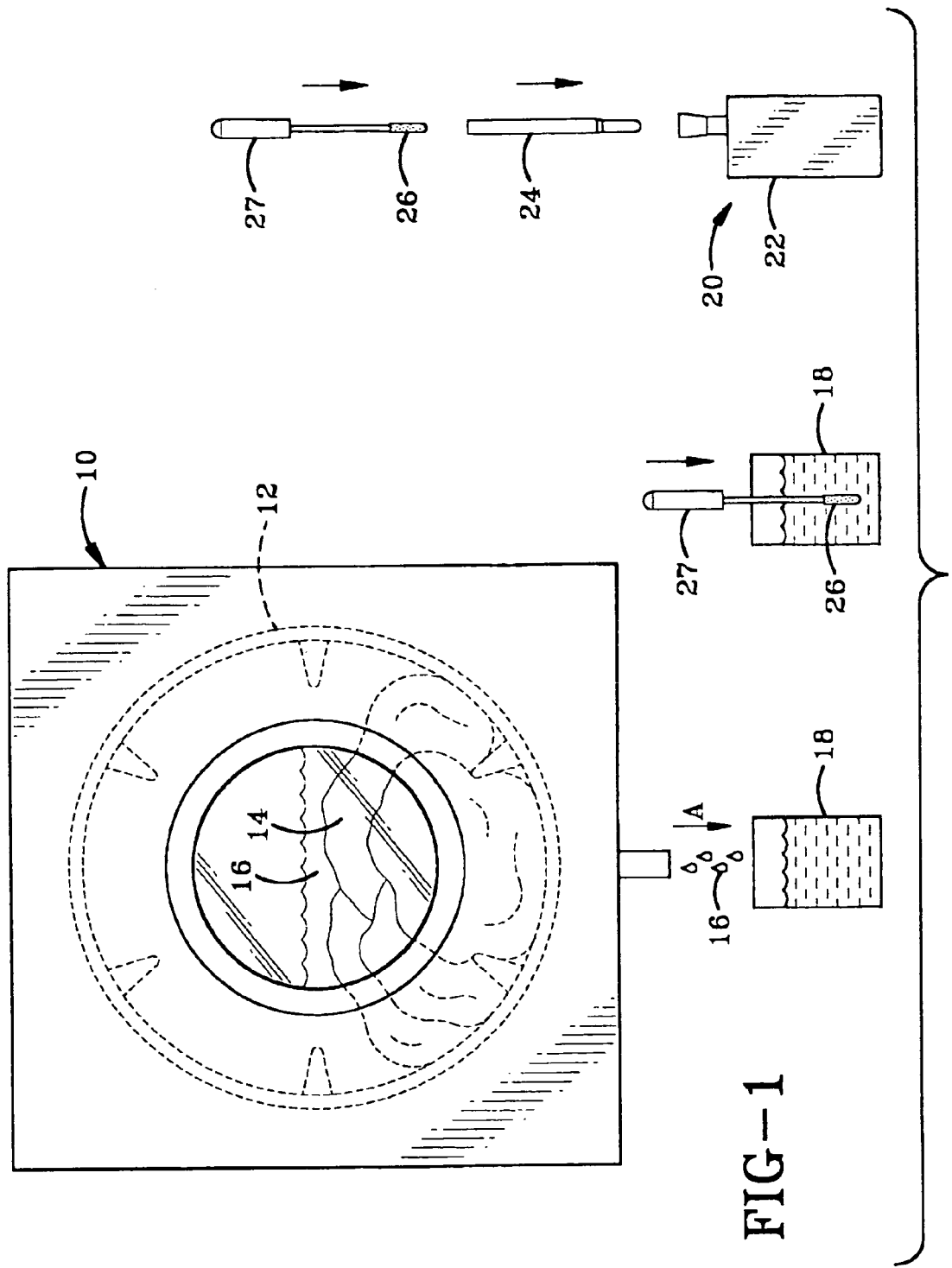
FIG. 1 is a diagrammatic view of a washing machine and a testing device for testing the water solution drained from within the washing machine.
Figure 2:
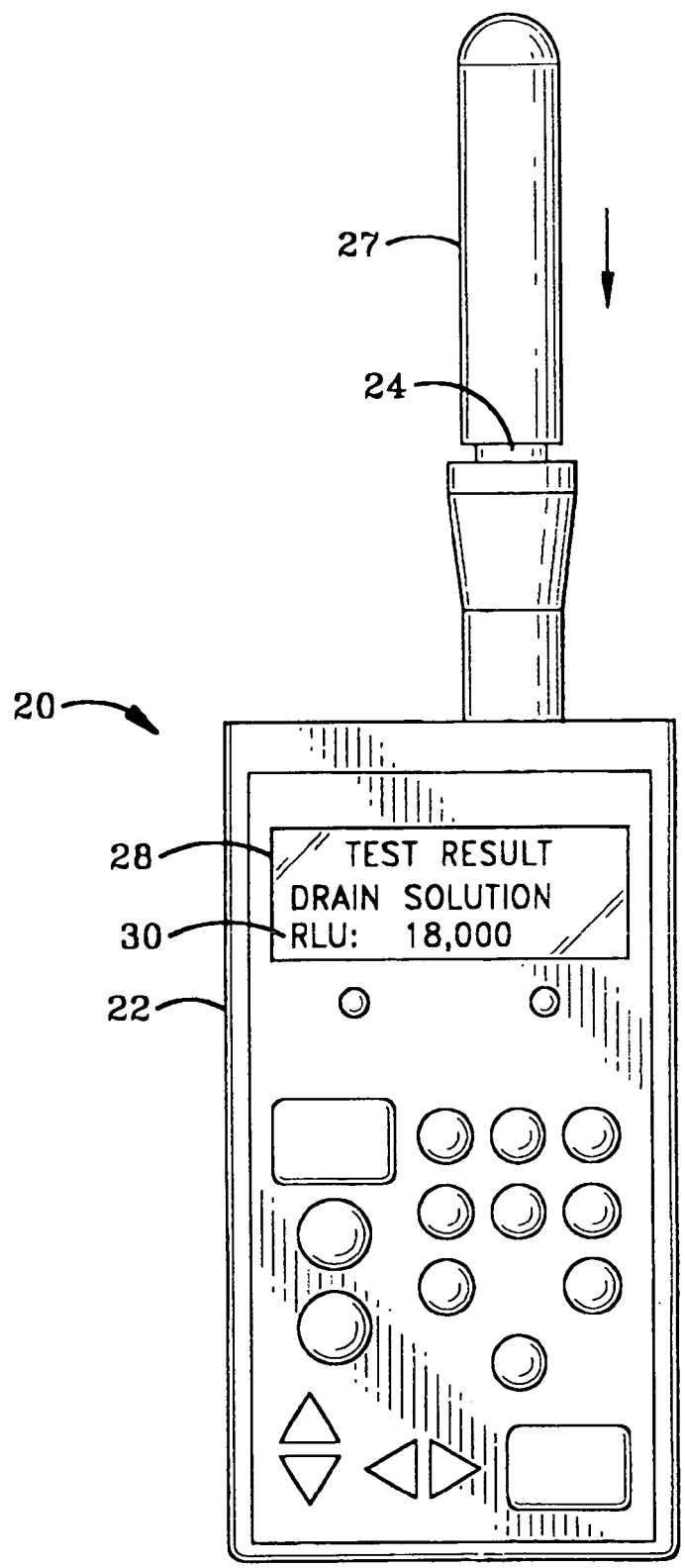
FIG. 2 is a diagrammatic view of the testing device.

FIG. 1 shows a cleaning device in the form of a washing machine or washer 10 having a cleaning vessel in the form of a rotatable drum 12 which defines a washer compartment therein in which laundry or textiles 14 may be placed for washing in a water solution 16 which may contain various detergents and chemicals suitable to promote the cleaning of textiles 14. Textiles 14 may be made up of various textiles such as aprons, butcher coats, sheets, towels, surgical garments, napkins, various other types of uniforms, linens, and so forth. A container or catch vessel 18 is disposed below washer 10 to catch the soiled or dirty water solution 16 which is drained (arrow A) from washer 10 subsequent to the washing or laundering of textiles 14. Vessel 18 is initially free of adenosine triphosphate (ATP) prior to catching the soiled water solution 16, commonly known as sour drain.

Washing textiles 14 in washer 10 is not the only method or device for cleaning textiles 14, and the process shown in the figures is meant to represent the cleaning of textiles by any method using a water solution. For example, dry cleaning utilizes a water solution having dry cleaning chemicals therein to achieve the cleaning process. The present test method may be used to test the used water solution from the dry cleaning process as well. In addition, newly manufactured textiles are typically cleaned by dipping them in a cleaning solution at the manufacturing textile mill. At least the final solution used in this cleaning process involves a water solution which may also be tested by the present method.

An ATP tester 20 is used to test the drained solution 16. In the exemplary embodiment, tester 20 includes a luminometer 22, a sample cylinder 24 and a swab 26 which is removably insertable into cylinder 24 and held by handle 27. Depending on the specific test, the cylinder and/or swab may be inserted into the luminometer 22, or, for instance, a portion of cylinder 24 may be inserted into luminometer 22. One such tester is described in the afore mentioned U.S. Pat. No. 6,180,395, which as previously mentioned is incorporated herein by reference. Such testing devices are sold by Charm Sciences, Inc. of Malden Mass. under the names POCKETSWAB® Plus, WATERGIENE® and ALLERGIENE®. Another portable swab-type device used in an ATP bioluminescent test is sold under the name LIGHTNING® by Idexx Laboratories, Inc. of Westbrook, Me.

These swab-type devices typically have a pre-moistened swab for gathering a test sample which is mixed within a tube such as cylinder 24 with a buffer solution and luciferin-luciferase test reagents which provides for bioluminescence which is read by the luminometer in relative light units (RLU). The POCKETSWAB® device utilizes a buffer to facilitate the rapid release of ATP from any organic source including micro-organisms and a neutralizer buffer for optimizing the luciferin-luciferase reaction.

Various other ATP tests are also available. Other bioluminescent ATP tests include one which is described in "The Handbook of ATP-Hygiene Monitoring" by Bio-Orbit Oy of Turku, Finland; and one known as the Charm ABC Swab Test sold by the above referenced Charm Sciences, Inc.

As further shown in FIG. 1, swab 26 is dipped in or otherwise wetted by the drained water solution 16, reinserted into cylinder 24 and mixed with the appropriate buffer solution and luciferin-luciferase reagents in order to provide the bioluminescence which is then measured by luminometer 22. FIG. 2 shows that luminometer 22 has a display 28 on which is displayed a specific read out or result 30 of the ATP detected from swab 26, measured in RLU's. Once the sample is placed in luminometer 22, it takes only about five seconds to obtain result 30. A predetermined acceptable level of ATP is typically stored within luminometer 22 and compared with result 30 so that luminometer 22 may also display a pass or fail indication.

If the ATP level is below the acceptable predetermined value, textiles 14 are then removed from washer 10 and dried in a dryer typically heated by a gas or electric heat source. This may be followed by various finishing steps, such as ironing, pressing, steaming such as through a steam tunnel, and the hanging of textiles such as garments on hangers and enclosure of the textiles within bags, boxes or the like. Preferably, no additional sanitizing steps are required after removing the textiles from the washer, as detailed further below.

However, if the ATP level is greater than the acceptable value, textiles 14 will be re-washed or otherwise additionally cleaned and retested in the same manner until the test result is within an acceptable range. Typically, textiles 14 go through multiple cleaning or washing cycles which include washing, draining, rinsing and possibly extraction by centrifuge or the spinning of drum 12 at relatively high speeds. Based on previous testing and general knowledge within the field, personnel within the field of laundering may already know that for a given type of textiles, it will take a certain number of washes and rinses in order to approach the degree of sanitation desired. Thus, a given load of textiles may be washed and rinsed more than once and often many times before the drain water solution is tested for ATP. Because the various types of tests used in the present invention are relatively quick, generally taking no more than five or ten minutes and potentially even less, the testing of the drained water solution will normally be done while the textiles remain in the washer. Preferably, the testing period takes no more than 15 minutes.

Figure 3:
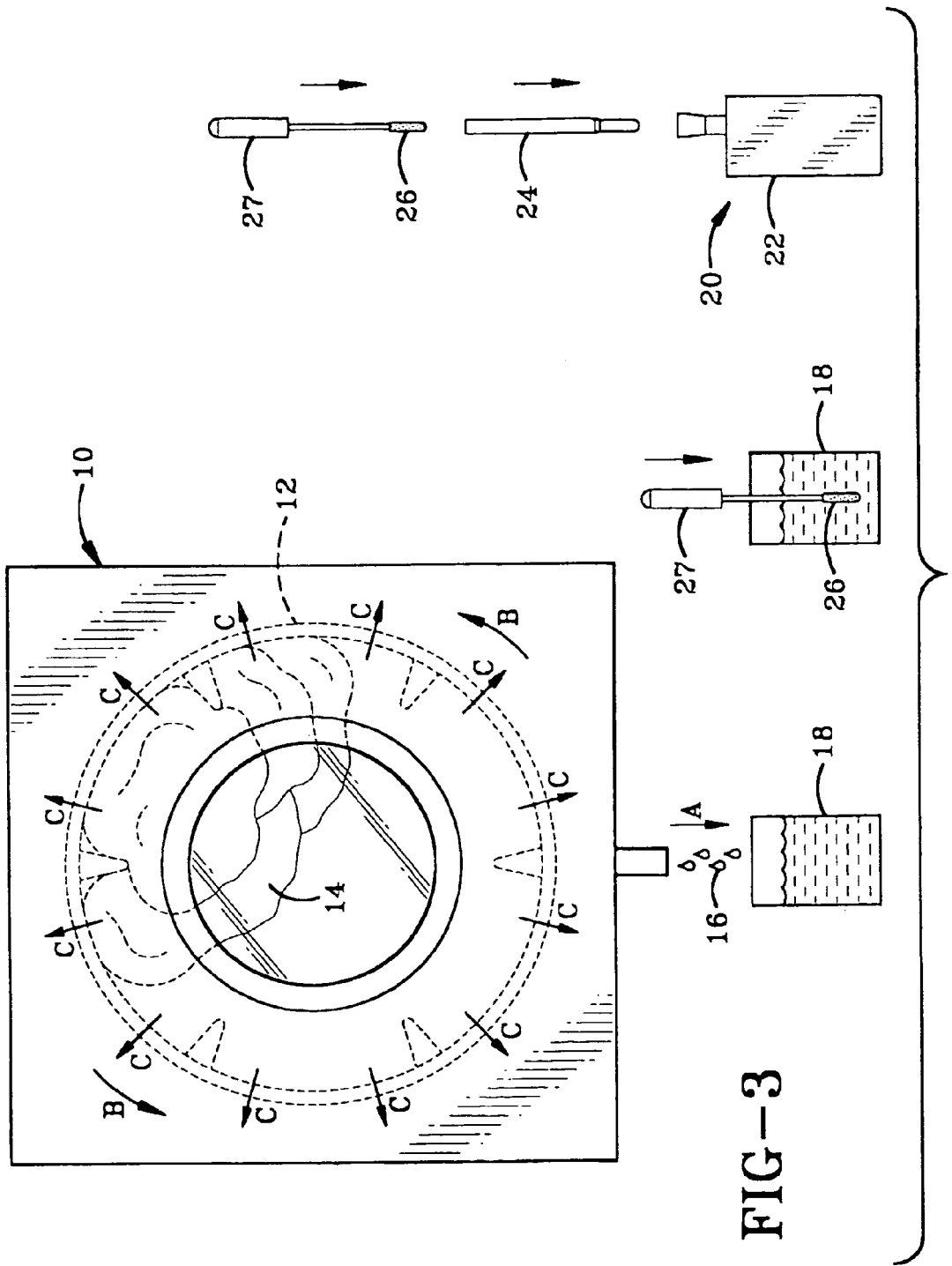
FIG. 3 is similar to FIG. 1 and shows additional water solution being extracted from the drained textiles and the testing of the extracted water solution.

Referring to FIG. 3, the second method of testing is described. The second method is very similar to the first method except that the water solution which is tested is that which is extracted from textiles 14 after the standard drain of solution 16 by gravity and/or pumping thereof. More particularly, drum 12 goes through a spinning cycle, or is rotated at relatively high speeds in order to extract additional water solution 16 from textiles 14 via a centrifuge effect or centrifugal force. Rotation of drum 12 is shown at arrows B and the extracted solution is indicated at arrow C. The extracted solution 16 is then drained into vessel 18 and tested in the same manner as described above.

TABLE 1

Comparison of Test Locations

| Test Location | Dry Soiled Textile | Test Vessel | Washer Drain |
|---|---|---|---|
| ATP (RLU) | 173,387 | 835,793 | 5,444,266 |
| Hach Test Kit (CFU) | <100 | 100,000 | 1,000,000 |

Table 1 Notes:
1. The "dry soiled textile" test was performed prior to being washed; the "test vessel" test was of soiled water solution extracted from a textile which was placed in a water solution in a vessel and stirred or slightly agitated; and the "washer drain" test was a test of soiled water solution drained from the washer in which the textile was washed, the latter being indicative of a high degree of agitation.
2. All ATP results from a swab method with readings from a NOVALUM ® luminometer.
3. Hach Test Kit readings were taken after 48 hours of bacterial growth and reported as colony-forming units (CFU). In particular, the tests were done with a Hach Paddle Tester, Total Aerobic Bacteria/Disinfection Control Test Kit sold by the Hach Company of Loveland, CO.

Table 1 primarily shows that the test of the dry soiled textile is generally inaccurate and thus may be misleading. As will be appreciated, even when the test of the dry textile is performed with a pre-moistened swab, the testing of the textile directly, especially when dry, is essentially a surface test which will not indicate the level of ATP or various contaminants further entrapped within the fibers of the cloth. The "test vessel" test shows that even a small degree of agitation of the dirty textile in a water solution allows various contaminants to be released or extracted therefrom to a notably greater degree than possible from the swabbing of the dry soiled textile. The soiled washer drain solution shows a far greater amount of ATP which is in keeping with the ability of the high-agitation washer to strip all sorts of contaminants from the fabric via mechanical action, solubility in water and/or the entrainment of the contaminants in the water solution.

The results from the Hach test kit provide a similar comparison. In addition, the test results from the Hach test kit indicate that the dry soiled textile may actually be within an acceptable range of sanitation which would be expected only subsequent to the textile being washed. The results from Table 1 thus emphasize the need for a test which better establishes a more accurate reading of the ATP level in the textiles.

TABLE 2

ATP Test Results of Various Textile Types

| Washer | Max. Capacity (lbs. clean dry cotton) | Textile Type | No. of Steps | Sour Drain Test (RLU) | Wet Textile Test (RLU) |
|---|---|---|---|---|---|
| #1 | 450 | white industrial | 21 | 39624 | 0 |
| #2 | 450 | 65/35 shirts | 17 | 9510 | — |
| #3 | 600 | colored cotton | 15 | 40000 | 0 |

TABLE 2-continued

ATP Test Results of Various Textile Types

| Washer | Max. Capacity (lbs. clean dry cotton) | Textile Type | No. of Steps | Sour Drain Test (RLU) | Wet Textile Test (RLU) |
|---|---|---|---|---|---|
| #4 | 600 | 65/35 pants | 13 | 18034 | 0 |

Table 2 Notes:
1. The term "65/35" stands for 65% polyester and 35% cotton; typically, the white industrial textile type is of a 65/35 blend.
2. The number of steps typically includes a combination of washing, draining, rinsing and spinning in various orders depending on the textile type.
3. Tests performed via POCKETSWAB ® Plus method with readings provided by a NOVALUM ® luminometer.
4. In the sour drain test, the swab was wetted with the soiled water solution drained from the washer after the final step indicated in the number of steps column.
5. In the wet textile test, the swab was rubbed on the wet textile which was still wet with the water solution of the wash after the final step of washing.

As Table 2 shows with reference to the POCKETSWAB® Plus test, even when the sour drain test gave an ATP reading of 40,000 RLU, the test of the wet textile gave an ATP reading of 0 RLU. This further emphasizes the difficulty of obtaining an accurate result concerning the level of contaminants via the direct swabbing of a textile.

If the textiles are sufficiently clean at the end of the washing or other cleaning process, there is no need, absent any re-contamination of textiles, for additional sanitizing steps thereafter. This is the most preferred condition of the textiles subsequent to washing or other cleaning in order to eliminate these additional sanitizing steps which may be relatively costly. Thus, it is preferred to maintain the textiles in a sanitary condition during the process of drying and all of the finishing steps and delivery to the customer or user of the textiles without additional sanitization.

Applicant's method of ATP testing thus provides a more accurate indicator of the level of ATP and associated bacteria of laundered textiles than do tests based on the direct swabbing of the textile. In addition, the textiles are tested for ATP at an earlier stage of the laundering process which can avoid the unnecessary repetition of various steps of the laundering process. Moreover, the present method may eliminate the need for sanitizing procedures subsequent to the washing or other cleaning process while maintaining a level of sanitation equal to or better than that of the prior art methods.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention is an example and the invention is not limited to the exact details shown or described.

The invention claimed is:

1. A method comprising the steps of:
   cleaning textiles with a first water solution whereby the water solution becomes used;
   draining the first used water solution;
   cleaning the textiles after the step of draining with a second water solution whereby the second water solution becomes used; and
   testing the second used water solution for the presence of any adenosine triphosphate (ATP) in the second used water solution which was extracted from the textiles to determine whether the textiles are sufficiently clean.

2. The method of claim 1 wherein the steps of cleaning occur in a cleaning vessel; and the step of testing comprises the step of testing the second used water solution for the presence of ATP while the textiles remain in the cleaning vessel.

3. The method of claim 2 further comprising the step of cleaning the textiles further with a subsequent water solution if an amount of the ATP detected in the step of testing exceeds a predetermined acceptable level.

4. The method of claim 3 further comprising the step of testing the subsequent water solution for the presence of ATP.

5. The method of claim 4 further comprising the step of removing the textiles from the cleaning vessel if an amount of the ATP detected in the step of testing the subsequent water solution does not exceed the predetermined acceptable level.

6. The method of claim 2 further comprising the step of removing the textiles from the cleaning vessel if an amount of the ATP detected in the step of testing does not exceed a predetermined acceptable level.

7. The method of claim 6 further comprising, absent re-contamination of the textiles, the steps of drying and finishing the cleaned textiles to a degree suitable for delivery to a user of the textiles without further sanitizing the textiles after the step of removing.

8. The method of claim 1 wherein the step of cleaning the textiles with the second water solution comprises the step of cleaning textiles with the second water solution in a cleaning vessel whereby the second water solution becomes used; further comprising the step of draining the second used water solution from the cleaning vessel; and wherein the step of testing comprises the step of testing the drained second water solution.

9. The method of claim 8 wherein the step of draining the second used water solution comprises the step of draining the second used water solution by force of gravity from the cleaning vessel.

10. The method of claim 1 wherein the step of cleaning the textiles with the second water solution comprises the step of cleaning the textiles with the second water solution in a cleaning vessel whereby the second water solution becomes used; further comprising the steps of draining the second used water solution by force of gravity from the cleaning vessel; and extracting a further amount of the second used water solution from the drained textiles by a method other than by force of gravity; and wherein the step of testing comprises the step of testing the extracted water solution.

11. The method of claim 10 wherein the step of extracting comprises the step of spinning the textiles to release the further amount of the used water solution by centrifugal force.

12. The method of claim 1 wherein the step of testing comprises the step of testing the second water solution for the presence of ATP without testing the first water solution for the presence of ATP.

13. The method of claim 1 wherein the step of testing comprises the step of assaying the second used water solution for the presence of ATP by mixing the second used water solution with luciferase and luciferin.

14. The method of claim 1 wherein the step of testing comprises the step of assaying the second used water solution for the presence of ATP by mixing the second used water solution with a buffer which accelerates the release of ATP.

15. The method of claim 1 wherein the step of testing comprises the step of testing the second used water solution for the presence of ATP with a luminometer.

16. The method of claim 15 further comprising the steps of wetting a swab with the second used water solution; and creating a bioluminescent reaction with the second used water solution from the wetted swab which is detectable by the luminometer.

17. The method of claim 1 wherein the step of testing is performed before the textiles are dried.

18. The method of claim 1 wherein the step of cleaning the textiles with the second water solution comprises the step of cleaning textiles with the second water solution in a cleaning vessel whereby the second water solution becomes used; further comprising the step of pumping the second used water solution out of the cleaning vessel; and wherein the step of testing comprises the step of testing the pumped second used water solution.

19. The method of claim 8 wherein the step of cleaning the textiles with the second water solution comprises the step of cleaning textiles with the second water solution in a cleaning vessel of a washing machine whereby the second water solution becomes used; the step of draining comprises the step of draining the second used water solution from the cleaning vessel through a drain of the washing machine; and the step of testing comprises the step of testing the drained second used water solution.

20. The method of claim 8 further comprising the step of catching in a catch vessel the second used water solution drained from the cleaning vessel; and wherein the step of testing comprises the step of testing the second used water solution caught in the catch vessel.

21. The method of claim 20 wherein the step of catching comprises the step of catching in a catch vessel disposed below the cleaning vessel the second used water solution drained from the cleaning vessel.

22. The method of claim 20 wherein the catch vessel is free of ATP prior to the step of catching.

\* \* \* \* \*